United States Patent
Desai et al.

(10) Patent No.: US 6,638,728 B1
(45) Date of Patent: Oct. 28, 2003

(54) COATED SURFACES WITH HIGH CAPACITY FOR CAPTURING TARGET MOLECULES

(75) Inventors: Surbhi Desai, Rockford, IL (US); Mark Rickerd, Marengo, IL (US); Ineabel Horneij, Rockford, IL (US)

(73) Assignee: Pierce Biotechnology, Inc., Rockford, IL (US)

(*) Notice: Subject to any disclaimer, the term of this patent is extended or adjusted under 35 U.S.C. 154(b) by 2 days.

(21) Appl. No.: 09/883,100

(22) Filed: Jun. 15, 2001

Related U.S. Application Data

(60) Provisional application No. 60/212,033, filed on Jun. 16, 2000.

(51) Int. Cl.[7] .............................................. G01N 33/543
(52) U.S. Cl. ........................... 435/7.5; 422/56; 422/57; 435/287.9; 435/805; 435/810; 435/969; 435/970; 436/518; 436/531

(58) Field of Search ..................... 422/56, 57; 435/7.5, 435/287.9, 805, 810, 969, 970; 436/518, 531

(56) References Cited

U.S. PATENT DOCUMENTS

| | | | | |
|---|---|---|---|---|
| 4,478,914 A | * | 10/1984 | Giese | 428/407 |
| 4,496,654 A | * | 1/1985 | Katz et al. | 422/56 |
| 4,656,252 A | * | 4/1987 | Giese | 530/350 |
| 5,276,062 A | * | 1/1994 | Haase | 521/25 |
| 6,270,983 B1 | * | 8/2001 | Strohner et al. | 435/7.5 |

* cited by examiner

Primary Examiner—Christopher L. Chin

(57) ABSTRACT

New protein coated surfaces, which have a high capacity for capturing target molecules, thus yielding assays with enhanced sensitivity, are disclosed. Surfaces prepared according to the present invention contain a coating consisting essentially of streptavidin, avidin or "NeutrAvidin" in polymeric form, wherein polymerization has been controlled to an extent such that the polymer is predominantly dimers, trimers and tetramers of the native molecule.

12 Claims, 1 Drawing Sheet

COATED SURFACES WITH HIGH CAPACITY FOR CAPTURING TARGET MOLECULES

RELATED APPLICATIONS

This application claims priority from U.S. Provisional Application No. 60/212,033, filed Jun. 16, 2000.

FIELD OF INVENTION

The present invention relates to surfaces, such as those of multiwell or microtiter plates, coated with proteins useful as capturing devices for antigens, antibodies and the like and, more particularly, to surfaces coated with polymerized streptavidin, avidin or NeutrAvidin™ deglycosylated avidin.

BACKGROUND OF THE INVENTION

Proteins coated on various solid surfaces are used as capturing devices for antigens, antibodies, ligands, receptors, oligonuceotides, and the like target molecules. In some cases the capturing molecules are bound directly to the surface and in other cases they are bound indirectly using, for instance, techniques based on avidin-biotin chemistry.

Solid surfaces to which the proteins are bound can be polystyrene, polypropylene, or membranes. The surfaces typically are located on the inside of tubes or the wells of plates such as microwell or microtiter plates, the bottoms of filter plates or the outside surfaces of spheres.

Microwell polystyrene plates coated with various proteins are commercially available. In particular, plates coated with streptravidin are used as tools in certain high throughput screening applications. For example, they are used to capture biotinylated antigens or antibodies. Applications in conventional ELISA use is also found in binding biotinylated oligonucleotides or PCR products in hybridization assays.

Streptavidin coated plates can be prepared by simply adsorbing the protein, in native form, onto the plate. The protein is commonly dissolved in a buffer, e.g., a carbonate/bicarbonate buffer, at a pH above 9.0 and then applied to the plates and dried. However, when the plates are so coated with native streptavidin only a limited number of protein molecules are bound or otherwise available to capture target molecules. In turn, the plates have a low capacity for capturing the intended target molecule. This results in diminished sensitivity of the assay and, accordingly, there is a need to increase the capacity of such coated plates and surfaces.

SUMMARY OF INVENTION

Now, in accordance with the present invention, there are provided new protein coated surfaces, which have a high capacity for capturing target molecules, thus yielding assays with enhanced sensitivity. Also, in connection therewith, assays using the coated surfaces provided by the present invention have an extended linear working range, particularly when the target molecules are small in size.

Surfaces prepared according to the present invention having the attributes identified above contain a coating consisting essentially of streptavidin, avidin or NeutrAvidin™ deglycosylated avidin in polymeric form, wherein polymerization has been controlled to an extent such that the polymer is predominantly, i.e., greater than 50%, and generally at least 60%, dimers, trimers and tetramers of the native molecule. The extent of polymerization can be determined by SDS-PAGE electrophoresis. As used herein, the term "consisting essentially of" means that the coating contains the identified native molecules in polymeric form, but does not exclude the presence of a minor amount of native monomer.

In a preferred aspect of this invention, utilizing a coating buffer containing a lyotropic salt, such as potassium sulfate, at about neutral pH enhances coating of the polymerized protein onto a surface.

DETAILED DESCRIPTION

Figure 1:
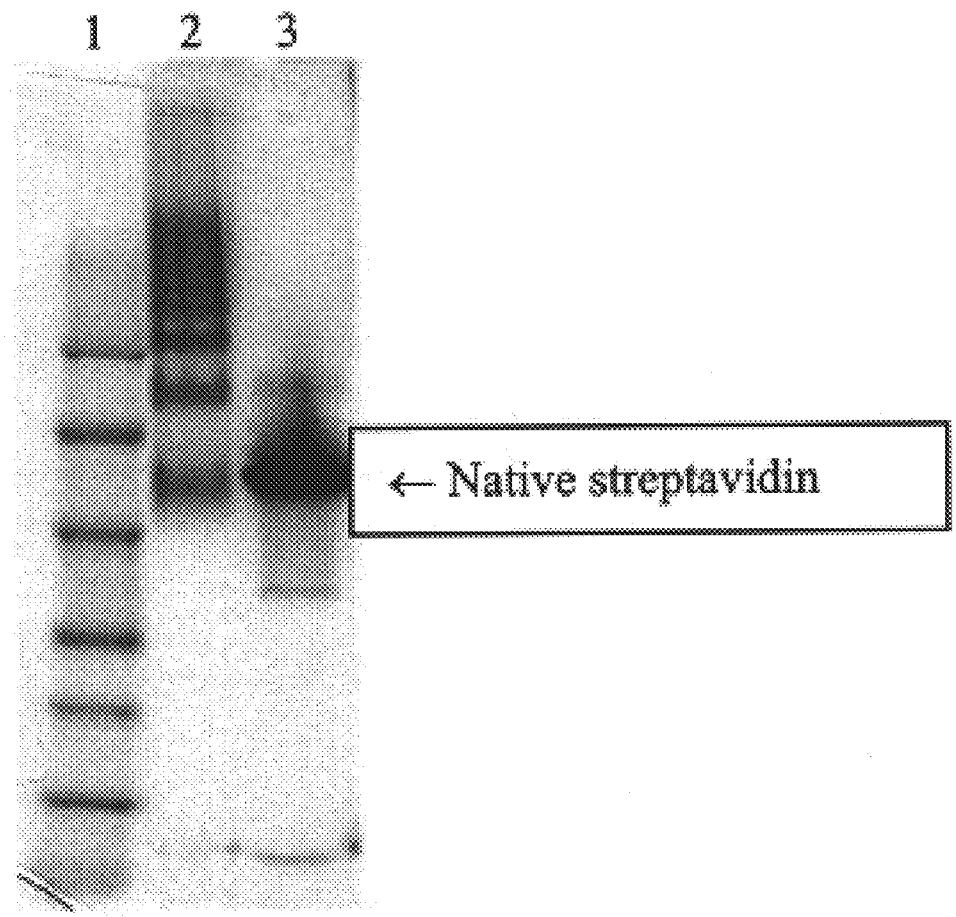
FIG. 1 depicts a SDS-PAGE separation illustrating that the polymer (in non-reduced form) prepared in Example I is composed predominantly of dimers, trimers and tetramers.

In preparing the polymerized protein used as the capturing coating in accordance with the present invention, a portion of the protein (in monomer form) molecules is first reacted with a reagent having bi-functional capability, but only one function of which initially reacts with the molecules. A second portion of the monomeric protein molecules is then reacted with a second reagent, again having bi-functional capability, but with only one function thereof initially reacting with the protein. As to the unreacted functionalities of the two reagents, they should be such that they can react together directly or react together with additional treatment. As used herein, the streptavidin and avidin monomers are tetrameric molecules having about a 67,000 Dalton molecular weight. NeutrAvidin™ deglycosylated avidin is a biotin binding protein available from Pierce Chemical Company which is avidin that has been deglycosylated to neutralize charge.

On combining the two monomer portions of the protein, modified as above with their bi-functional reagents, polymerization, i.e., cross linking, of the two portions of monomeric protein molecules occurs. There are a variety of bi-functional reagents which are useful herein. Such reagents are identified in "Bioconjugate Techniques" authored by Hermanson and published by Academic Press, the disclosure of which is incorporated herein by reference.

The degree of polymerization is principally dependent upon the amount of bi-functional reagent initially reacted with each portion of monomeric protein molecules, the reaction ratio between the two portions of molecules of the modified monomers, and the elapsed time of the polymerization reaction. In general, a molar ratio of cross-linking reagent to monomer of at least about 5 to 1, and preferably 10 to 1 has been found useful with the molar ratio of monomers reacted being about equal. Polymerization reaction times of about 1–2 hours can be used. However, conditions of reaction such as pH, temperature and time as well as selection of cross-linking agents can influence the preparation of useful polymer mixtures.

To achieve the desired degree of polymerization, i.e., the presence of predominantly dimers, trimers and tetramers, polymerization should be achieved to the point where the polymerized product remains in solution, and the solution may become distinctly hazy in appearance, but the protein polymer does not precipitate or form large insoluble aggregates.

The following examples illustrate the present invention.

EXAMPLE I 10 mg of Streptavidin monomer dissolved at 10 mg/ml in 100 mM sodium phosphate buffer containing 150 mM NaCl, pH 7.2 (PBS) was derivatized with a 10M excess of the bifunctional reagent, N-Succinimidyl-A-acetylthioacetate (SATA), dissolved at 40 mg/ml in Dimethyl formamide, (DMF) for 2 hours. At the same time 10 mg of Streptavidin dissolved at 10 mg/ml in PBS was derivatized with a 10 M excess of the bifunctional reagent, Sulfosuccinimidyl 4-(N-maleimidomethyl) cyclohexane-1-carboxylate (Sulfo-SMCC), dissolved at 40 mg/mi in water for 1 hour. The samples were purified to remove excess bi-functional reagents using 10 mL crosslinked dextran desalting columns. The purified samples were combined in equal molar ratios and degassed under vacuum. The combined volume was determined and then a quantity of 1 M Hydroxylamine Hydrochloride, previously degassed under vacuum, was added so that the final concentration of the Hydroxylamine Hydrochloride in the sample was 50 mM. The addition of Hydroxylamine Hydrochloride deblocks the acetylated sulfhydyl group on the SATA modified protein creating a free sulfhydyl group to react with the maleimide groups on the Sulf-SMCC modified proteins. The reaction was carried out for 1 hour and 30 minutes at room temperature. Excess maleimide groups were capped with β-mercaptoethanol for 15 minutes. Excess sulfhydryl groups were capped with N-ethylmaleimide for 15 minutes. Then the sample was dialyzed against 5 L of PBS.

SDS-PAGE electrophoresis (4–20% Tris-Glycine gel; non-reducing condition) of the sample confirmed that the polymer was about 60% combined dimer, trimer and tetramer. This is illustrated in FIG. 1 wherein Lane 1 is a separation of pre-stained protein molecular weight markers, Lane 2 is a separation of streptavidin polymer prepared in accordance with this Example and Lane 3 is separation of native Streptavidin. The molecular weight(kd) of the marker proteins are as follows: starting from the top 155; 84; 60; 39; 28; 18 and 9, respectively.

The 0D 280 of the sample was determined and the protein concentration of sample was adjusted so that the concentration was 50 µg/mL in a 50 mM sodium phosphate, 0.5M potassium sulfate, pH 8.0 buffer. An extinction coefficient of 3.1 at 280 nm absorbance for a streptavidin polymer solution having a 1 mg/mL concentration was used to determine the final concentration. The protein polymer was then coated on 96-well clear polystyrene plates at 100 µL/well and incubated overnight at room temperature. The plates were then blocked by washing 3×200 µL with "SuperBlock" Blocking Buffer (Pierce Chemical Company). The plates were emptied by tapping on paper towels and allowed to dry for 30 minutes.

The biotin binding capacity of the plates prepared above was determined by an inhibition method using biotin and biotin-HRP (biotinylated horseradish peroxidase). The plates were washed 2×200 µL with PBS/0.05% Tween™ 20 detergent. A serial dilution was made across the plates of 10 nM/ml Biotin in PBS/0.05% Tween™ 20 detergent, added at 100 µL/well. The plates were incubated for 1 hour at room temperature and then washed 3×200 gL with PBS/0.05% Tween™ 20 detergent. The plates were then incubated with a 1:10,000 dilution of biotin-HRP (1 mg/ml) in PBS/0.05% Tween™ 20 detergent, added at 100 µL/well, for 1 hour at room temperature. The plates were washed 3×200 µL with PBS/0.05% Tween 20 and then incubated for 5 minutes with 100 µL 1-Step Turbo-TMB™ (Pierce Chemical Company). 100 µL 2M $H_2SO_4$ was added per well to stop the reactions. The plates were read at OD 450.

In comparison to plates prepared with nonpolymerized streptavidin, the binding capacity of the plates of this Example I was about 25 times greater.

EXAMPLE II 10 mg of NeutrAvidin™ deglycosylated avidin dissolved at 10 mg/ml in PBS was derivatized with a 10M excess of SATA, dissolved at 40 mg/ml in DMF, for 1 hour. At the same time 10 mg of NeutrAvidin™ deglycosylated avidin dissolved at 10 mg/ml in PBS was derivatized with a 10M excess of Sulfo-SMCC, dissolved at 40 mg/ml in water, by reacting for 1 hour. The samples were purified using 10 mL crosslinked dextran desalting columns. The purified samples were combined in equal molor ratios. The combined volume was determined and then a quantity of 1M Hydroxylamine Hydrochloride, previously degassed under vaccuum, was added for the purpose stated in Example I so that the concentration of the Hydroxylamine Hydrochloride was 50 mM. The reaction was carried out for 1 hour and 30 minutes at room temperature under vacuum. As in Example I, the reaction was quenched with β-mercaptoethanol for 15 minutes and the reaction capped with N-ethyl maleimide for 15 minutes. Then the sample was dialyzed against 5L of PBS.

The OD 280 of the sample was determined and the protein concentration of sample was adjusted so that the final concentration was 50 µg/mL in a 50 mM sodium phosphate, 0.5 M potassium sulfate, pH 8.0 buffer. An extinction coefficient of 1.66 at an absorbance of 280 nm for a NeutrAvidin™ deglycosylated avidin polymer solution having a 1 mg/mL concentration was used to determine the final concentration polymer solution having a 1 mg/mL concentration was used to determine the final concentration. The protein polymer was then coated on 96-well clear polystyrene plates at 100 µL/well and incubated overnight at room temperature. The plates were then blocked by washing 3×200 µL with "SuperBlock" Blocking Buffer from Pierce Chemical Company. The plates were emptied by tapping on paper towels and allowed to dry for 30 minutes.

The biotin capacity of plates prepared in this Example II were determined as described in Example I and compared with the binding capacity of plates coated with unpolymerized NeutrAvidin™ deglycosylated avidin. The plates of Example II exhibited a four-fold increase in binding capacity.

EXAMPLE III

This example illustrates the use of the plates prepared in Examples I, except white plates (96 well) were coated instead of clear plates. The illustrated assay compares, in a biotin phosphopeptide binding format, the effectiveness of the coated plates of the present invention to plates coated with the non polymerized protein. Coating of all plates was accomplished as described in the forgoing examples.

The coated plates (Example I and a plate coated with native streptavidin) were washed 2×200 µl with PBS/0.05% Tween™ 20 detergent. Tyrosine Kinase Peptide 2 (Pierce Chemical Company), biotinylated and phosphorylated was diluted using PBS/0.05% Tween™ 20 detergent. The dilution of the biotinylated phosphopeptide was made so that when 100 µL was added to the well, the range covered 0 to 15 pM/well. 100 µL of each dilution was added to Rows 1–12. The plates were incubated for 1 hour at room temperature. The plates were then washed 3×200 µl with PBS/ 0.05% Tween™ 20 detergent. Anti-Phosphotyrosine antibody was diluted 1:1000 in PBS/0.05% Tween 20. 100 µl of the diluted antibody was added to each well of each plate. The plates were incubated at 37° C. for 1 hour. The plates were washed 3×200 µl with PBS/0.05% Tween™ 20 detergent. Goat anti-Mouse, Fluorescein antibody (at 1 mg/ml) was diluted 1:667.5 in PBS/0.05% Tween™ 20 detergent.

100 μl of the diluted antibody was added to each well of each plate. The plates were washed 3×200 μl with PBS/0.05% Tween™ 20 detergent. The plates were read using a fluorescent plate reader with an excitation filter set at 485 nm and an emission filter at 538 nm.

In this Example the polymerized streptavidin plate of this invention demonstrated 70% higher capacity than the native streptavidin coated plate. This demonstrates that a greater signal is obtained with the plate of the present invention compared to the other plate.

EXAMPLE IV

This example illustrates the use of the plates prepared in Examples I, except white plates (96 well) were coated instead of clear plates. The illustrated assay compares, in a biotinylated oligonucleotide binding format, the effectiveness of the coated plates of the present invention (Example I) to plates coated with the non polymerized streptavidin. Coating of the plates was accomplished as described in the forgoing examples.

The coated plates were washed 2×200 μl with PBS/0.05% Tween™ 20 detergent. Biotinactincapture oligonucleotide was made up in PBS at a concentration of 1.25 μM. The diluted biotinylated oligonucleotide was added at 100 μL per well in Row 1 of the plates. A 1:1 serial dilution was made, using 100 μL PBS and 100 μL of the 1.25 μM biotinylated oligonucleotide in PBS from Row 2 to 11. Only PBS was added to the Row 12 wells of each plate. The plates were incubated for 1 hour at room temperature. The plates were washed 3×200 μl with PBS/0.05% Tween™ 20 detergent. North2South™ Hybridization Buffer (Pierce Chemical Company) was warmed to 55° C. The Fluoractincapture oligonucleotide was made up in the warmed hybridization buffer at a concentration of 625 nM. 100 μL of the diluted fluorescein labeled oligonucleotide was added to each well of each plate. The plates were incubated for 1 hour at room temperature. The plates were washed 2×200 μL with North2South™ Wash Buffer (Pierce Chemical Company). The plates were washed 1×200 μL with PBS. 100 μL of PBS was added to the plate wells and then the plates were read using a fluorescent plate reader with an excitation filter set at 485nm and an emission filter at 538 nm.

The oligonucleotide hybridization assay performed on these plates display a Signal to noise (S/N) ratio with polymerized streptavidin plate of this invention that is 12-fold higher native streptavidin coated plate. This assay confirms that a higher binding capacity and a greater dynamic range are obtained with the plate prepared in accordance with the present invention.

What is claimed is:

1. A surface containing a coating consisting essentially of, in polymeric form, streptavidin, avidin or a deglycosylated avidin wherein the polymer is greater than 50% of a combination of dimers, trimers and tetramers of the native molecule.

2. The surface of claim 1 wherein the polymer is polymerized streptavidin or a polymerized deglycosylated avidin.

3. The surface of claim 2 wherein the polymer is polymerized streptavidin.

4. The surface of claim 1 wherein the polymer is at least 60% of a combination of dimers, trimers and tetramers.

5. The surface of claim 4 wherein the polymer is polymerized streptavidin or a deglycosylated avidin.

6. The surface of claim 5 wherein the polymer is polymerized streptavidin.

7. A polystyrene surface containing a coating consisting essentially of, in polymeric form, streptavidin, avidin or a deglycosylated avidin, wherein the polymer is greater than 50% of a combination of dimers, trimers and tetramers of the native molecule.

8. The polystyrene surface of claim 7 wherein the polymer is polymerized streptavidin or a polymerized deglycosylated avidin.

9. The polystyrene surface of claim 8 wherein the polymer is polymerized streptavidin.

10. The polystyrene surface of claim 7 wherein the polymer is at least 60% of a combination of dimers, trimers and tetramers.

11. The polystyrene surface of claim 10 wherein the polymer is polymerized streptavidin or a polymerized deglycosylated avidin.

12. The polystyrene surface of claim 11 wherein the polymer is polymerized streptavidin.

* * * * *